US012533494B2

(12) United States Patent
Pierce

(10) Patent No.: US 12,533,494 B2
(45) Date of Patent: Jan. 27, 2026

(54) INTRAVASCULAR CATHETER AND METHOD OF USE

(71) Applicant: Pierce Holdings, FLP, Hawkinsville, GA (US)

(72) Inventor: Thomas Pierce, Hawkinsville, GA (US)

( * ) Notice: Subject to any disclaimer, the term of this patent is extended or adjusted under 35 U.S.C. 154(b) by 0 days.

(21) Appl. No.: 17/588,592

(22) Filed: Jan. 31, 2022

(65) Prior Publication Data

US 2022/0241561 A1 Aug. 4, 2022

Related U.S. Application Data

(60) Provisional application No. 63/143,422, filed on Jan. 29, 2021.

(51) Int. Cl.
*A61M 25/06* (2006.01)

(52) U.S. Cl.
CPC .... *A61M 25/0662* (2013.01); *A61M 25/0606* (2013.01); *A61M 2025/0681* (2013.01)

(58) Field of Classification Search
CPC ............ A61M 25/0662; A61M 25/065; A61M 25/0068; A61M 25/0606; A61M 2025/0681; A61M 2025/0687
See application file for complete search history.

(56) References Cited

U.S. PATENT DOCUMENTS

2010/0137804 A1 6/2010 Wiley
2012/0078175 A1* 3/2012 Vreeman ........... A61M 25/0069 604/528
2018/0093074 A1* 4/2018 Burkholz .......... A61M 25/0606
2018/0153579 A1* 6/2018 Ueda ........................ B24B 19/16
2018/0256862 A1* 9/2018 Bagwell ............. A61M 25/0113
2019/0038877 A1 2/2019 Isaacson et al.
2019/0160263 A1* 5/2019 Yokota .............. A61M 25/0606
2020/0376237 A1* 12/2020 Hayakawa ............ A61M 25/09

FOREIGN PATENT DOCUMENTS

| | | | | |
|---|---|---|---|---|
| DE | 0163320 | A1 * | 8/2003 | ............ A61M 25/00 |
| DE | 10163320 | A1 | 8/2003 | |
| EP | 2862591 | B1 | 9/2020 | |
| WO | 2007005386 | A1 | 1/2007 | |
| WO | 2007024986 | A2 | 3/2007 | |
| WO | 2018165157 | A1 | 9/2018 | |

OTHER PUBLICATIONS

International Preliminary Report on Patentability for PCT/US2022/014492 mailed Jul. 31, 2023.
International Search Report and Written Opinion for PCT/US2022/014492 mailed May 16, 2022.
Examination Report for Australian Application No. 2022212203 mailed Sep. 1, 2023.
Notice of Acceptance for Israel Application No. 307237 mailed Jan. 12, 2025.

* cited by examiner

*Primary Examiner* — Laura A Bouchelle
*Assistant Examiner* — Sarah Dympna Grasmeder
(74) *Attorney, Agent, or Firm* — Perilla Knox & Hildebrandt LLP; Stephanie Davy-Jow; Thomas Hildebrandt

(57) ABSTRACT

Disclosed are various embodiments for an intravascular catheter and methods of use. In one embodiment, an intravascular catheter and needle assembly comprises a catheter needle and a catheter sheath surrounding a portion of the catheter needle. The catheter sheath has an end for insertion that is angled between 5 and 85 degrees.

12 Claims, 6 Drawing Sheets

INTRAVASCULAR CATHETER AND METHOD OF USE

CROSS-REFERENCE TO RELATED APPLICATIONS

This application claims priority to, and the benefit of, U.S. Provisional Patent Application No. 63/143,422, entitled "INTRAVASCULAR CATHETER AND METHOD OF USE," filed on Jan. 29, 2021, which is incorporated herein by reference in its entirety.

BACKGROUND

Conventional catheters are generally round in cross-section, with a 90-degree end cut perpendicular to the needle. The catheter is still outside the vessel with conventional catheters when the needle first makes contact with the bloodstream and must be advanced with the needle-catheter combination until the catheter is also within the vessel. If one attempts to thread the catheter before it enters the vessel, the attempt fails. It also can fail if the needle punctures the opposite wall of the catheter while attempting to advance the needle-catheter combination far enough into the vessel to accomplish cannulation by the catheter.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

The present disclosure relates to an improvement to intravascular catheters, also referred to as cannulas. The intravascular catheters described herein are intended to provide temporary peripheral vascular access. Intravascular catheters, whether for intravenous or intraarterial use, have sharp steel needle, beveled on one side. The needle is inserted into the skin at an angle that closely parallels the skin. The catheter, which is over the needle, is slid off into the blood vessel after insertion of the needle-catheter combination, where it remains to administer fluids or medications into the blood vessel or to insert medical devices. The catheter is a flexible hollow tube made of latex, silicone, Teflon, or another material.

The embodiments of the present disclosure are configured to facilitate starting an intravascular line on the first attempt, at a higher rate than traditional needle catheters. The catheters described, for example, may correspond sterile medical devices intended for one-time use in patients requiring access to the peripheral vascular system for short-term use to sample blood, monitor blood pressure, or administer fluids or medications.

In various embodiments of the present disclosure, the catheter's end is different from the conventional 90-degree cut. For example, the catheter's end may have an approximately 45 to 60-degree cut, giving a more oval appearance. However, the end may vary from 5 degrees to 85 degrees based on application. By creating an angle at the end of the catheter, the catheter is inserted within the vessel when the needle penetrates the vessel, eliminating problems on attempted placement. These embodiments allow the tip of the catheter to be within the vessel at the time of "flashback" of blood, which will enable the catheter to be advanced immediately and eliminate multiple attempts. The needle is then removed upon insertion of the catheter.

In various embodiments, the catheter with an angled end may be manufactured in a sterile facility. For example, the catheter may be created with an angled end via three-dimensional printing or casting from a mold that incorporates the angled end. The catheter may then be attached to the needle such that the tip of the catheter enters the vessel at the time of "flashback" of blood. The catheters may be manufactured in various sizes based upon the size of the blood vessel and application. The catheter may be tapered, or thinned, at the end circumferentially so that it as it comes in contact with the needle distally such that it will allow for a smooth transition of the needle-catheter combination into the blood vessel.

Figure 1:
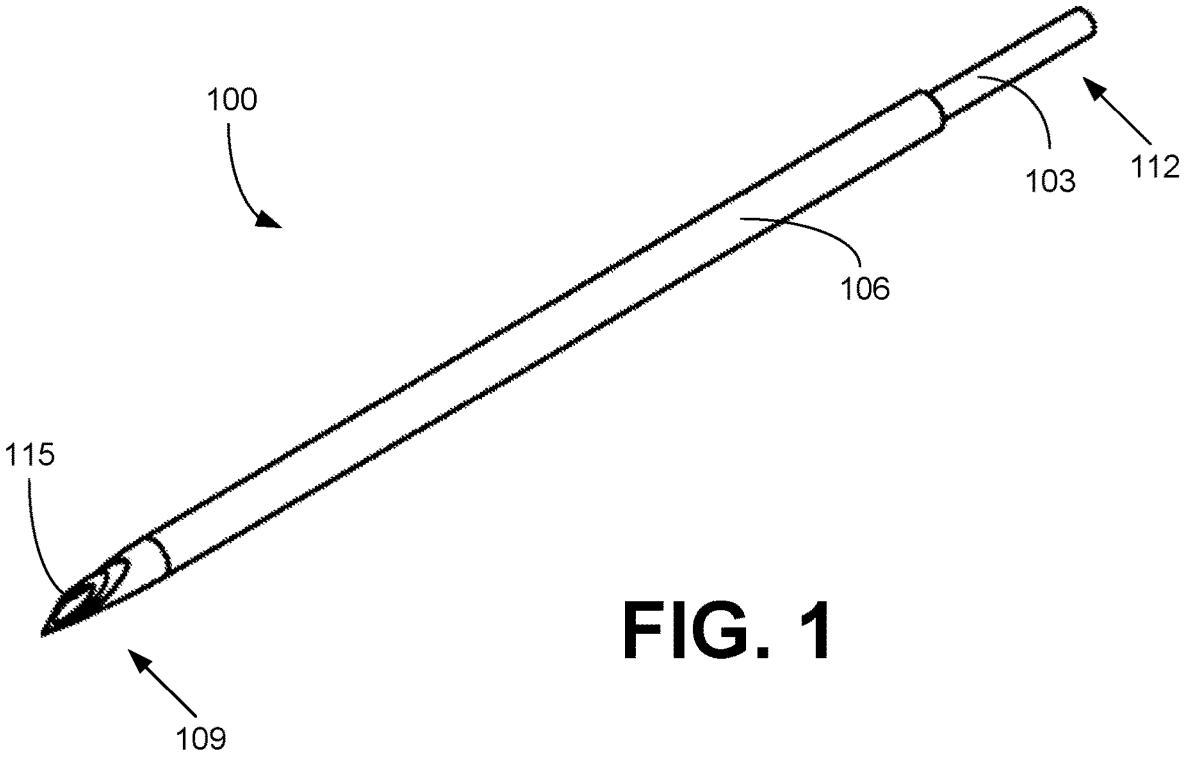
FIG. 1 is an isometric view of an intravascular catheter and needle according to one or more embodiments.

FIG. 1 is an isometric view of an intravascular catheter and needle assembly 100 according to one or more embodiments. The intravascular catheter and needle assembly 100 comprises a catheter needle 103 and a catheter sheath 106 that surrounds the catheter needle 103. For example, the catheter needle 103 may be made of stainless steel or another material, while the catheter sheath 106 may be made of polyurethane, polypropylene, rubber, or another material. Other components of the intravascular catheter and needle assembly 100 such as a catheter hub, a septum/valve, a needle hub, a safety clip, a septum opener, a septum housing, stabilizing wings, injection side port, anti reflux, etc., are omitted for simplicity.

The intravascular catheter and needle assembly 100 has an insertion end 109 and a proximal end 112. The insertion end 109 includes an exposed portion 115 of the catheter needle 103 that extends outwardly by some distance beyond the tip of the catheter sheath 106. Once the tip of the catheter needle 103 is inserted into a blood vessel, the catheter sheath 106 is fed into the blood vessel, and the catheter needle 103 is then withdrawn or retracted away from the blood vessel, through the catheter sheath 106, and finally removed from the catheter sheath 106.

Figure 2:
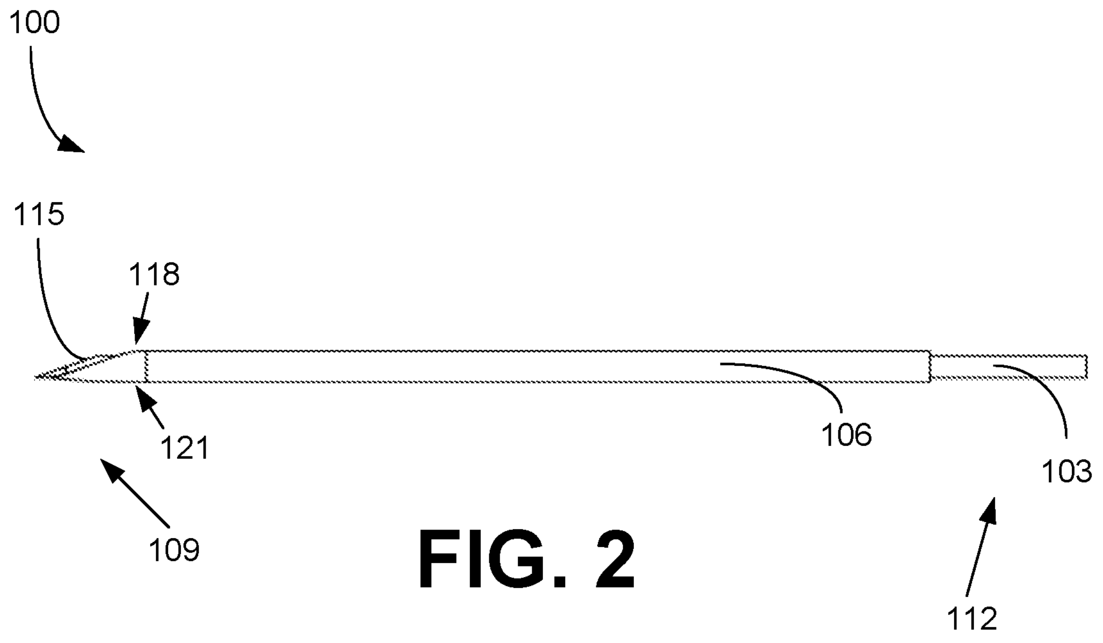
FIG. 2 is a side view of the intravascular catheter and needle according to one or more embodiments.

FIG. 2 is a side view of the intravascular catheter and needle assembly 100 according to one or more embodiments. In FIG. 2, the exposed portion 115 of the catheter needle 103 is more clearly seen. Also, in viewing the side profile, the tapers of both the catheter needle 103 and the catheter sheath 106 is shown. In this example, the taper of the catheter needle 103 approximately equals that of the taper of the catheter sheath 106 so as to be parallel or near parallel. Further, both the top surface 118 and the bottom surface 121 of the catheter sheath 106 are respectively tapered from a minimum thickness to a maximum thickness, but the taper angle is greater for the top surface 118 taper than the bottom surface 121 taper, which makes the bottom surface 121 taper more gradual than the top surface 118 taper. Overall, the design of the catheter sheath 106 gives the catheter sheath 106 a leading edge that may match the shape of the catheter needle 103 for proper alignment and to minimize the point of entry into the skin and into the blood vessel.

Figure 3:
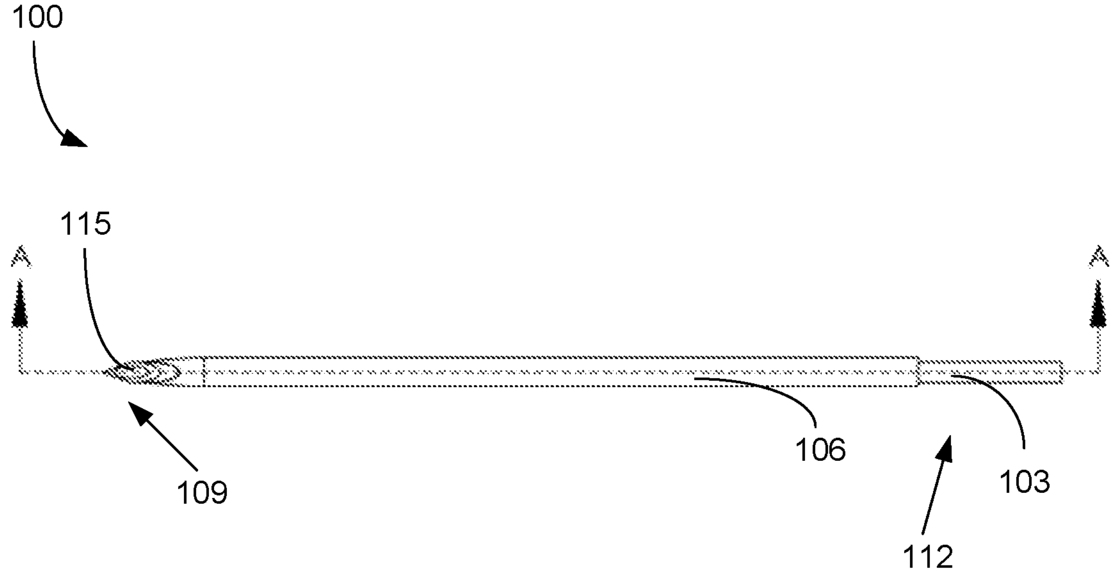
FIG. 3 is a top view of the intravascular catheter and needle according to one or more embodiments.

FIG. 3 is a top view of the intravascular catheter and needle assembly 100 according to one or more embodiments. FIG. 3 also defines a center line "A" as shown.

Figure 4:
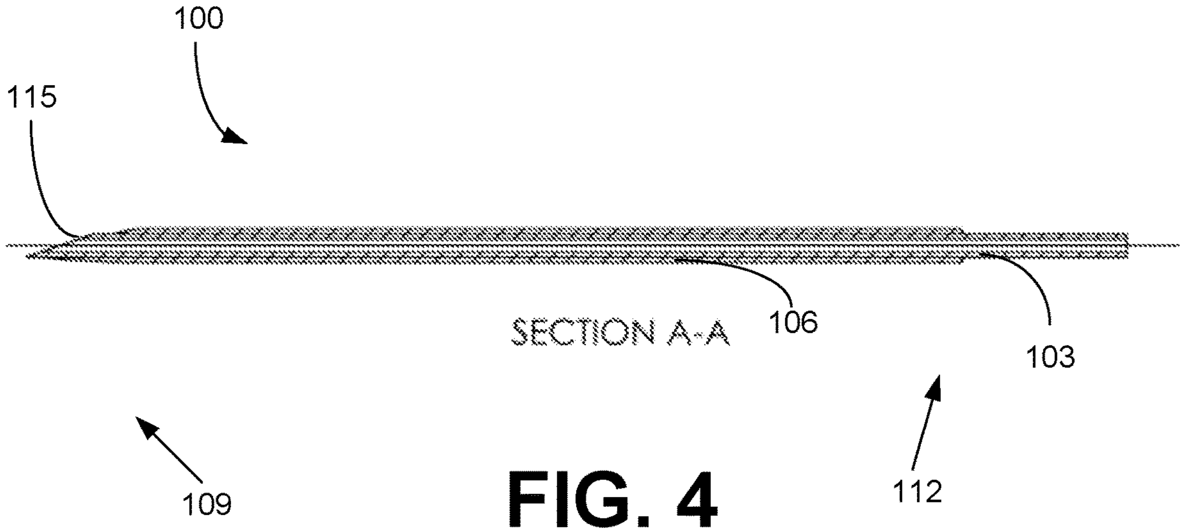
FIG. 4 is a cross-sectional view of the intravascular catheter and needle according to one or more embodiments.

FIG. 4 is a cross-sectional view of the intravascular catheter and needle assembly 100 according to one or more embodiments. FIG. 4 is a cross-section at the center line "A" shown in FIG. 3. Here, the internal channel of the catheter needle 103 can be seen along the center line.

Figure 5:
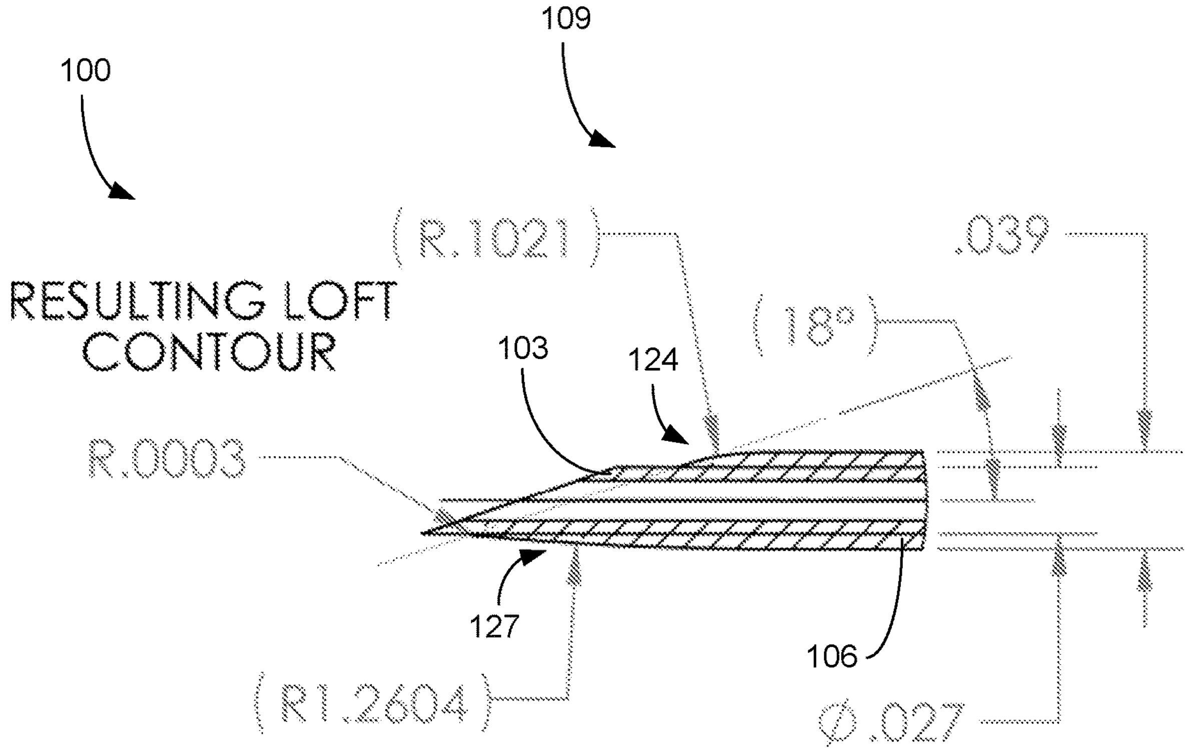
FIG. 5 is a detail view of the side profile of the insertion end of the intravascular catheter and needle showing sample dimensions and proportions of the characteristics of the tapers and diameters.

FIG. 5 is a detail view of the side profile of the insertion end 109 of the intravascular catheter and needle assembly 100 showing sample dimensions and proportions of the characteristics of the tapers and diameters. Specifically the differences in the top taper 124 versus the bottom taper 127 in the catheter sheath 106 are seen, where the top taper 124 is sharper, approximately along the overall taper and bevel of the catheter needle 103, e.g., 18 degrees. By contrast, the bottom taper 127 is more gradual; for example under 10 degrees. The inner diameter of the catheter sheath 106 is shown as 0.027 inches, while the outer diameter of the catheter sheath 106 is shown as 0.039 inches, both of which may be approximate values and may be multiplied by a constant to achieve a similar proportion if desired. The diameter dimensions may change along with the needle gauge. The catheter needle gauge can be sized from 14 and 24 gauge.

Figure 6:
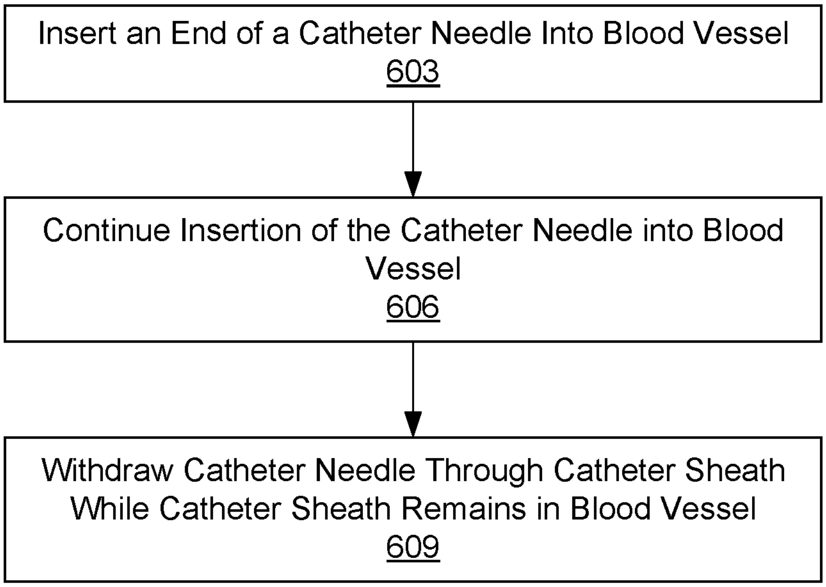
FIG. 6 is an example flowchart depicting steps of a method of use of the intravascular catheter and needle according to one or more embodiments.

FIG. 6 is an example flowchart depicting steps of a method of use of the intravascular catheter and needle assembly 100 according to one or more embodiments. A method of use may include more steps, different steps, fewer steps, or steps in different orders in various embodiments.

Beginning with box 603, a user inserts an end of the catheter needle 103 into a blood vessel. In box 606, the user continues insertion of the catheter needle 103 into the blood vessel until the end for insertion of the catheter sheath 106 that is angled is fully inserted into the blood vessel. Since the catheter sheath 106 is tapered and keyed to the catheter needle 106, it may be significant to avoid rotating the catheter sheath 106 when inserting the catheter sheath 106 as in conventional catheter insertion. Various embodiments may have a device (e.g., a ridge, a locking clip, a detent, etc.) to prevent rotation of the needle at the proximal end, for example, to maintain keying of the needle to the sheath. In box 609, the user withdraws the catheter needle 103 through the catheter sheath 106 while the catheter sheath 106 remains in the blood vessel.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. An intravascular catheter and needle assembly comprising:

a catheter needle having a bevel;

a catheter sheath surrounding a portion of the catheter needle, the catheter sheath having an end for insertion that is angled between 5 and 85 degrees, wherein the angle of the end for insertion is approximately parallel to a bevel angle of the catheter needle such that a leading edge of the catheter sheath matches a shape of the catheter needle so that the catheter sheath is inserted within a vessel when the catheter needle penetrates the vessel;

a top side of the catheter sheath, wherein the top side is tapered at approximately 18 degrees from the end for insertion;

a bottom side of the catheter sheath, wherein the bottom side is tapered at less than 10 degrees from the end for insertion; and wherein an internal channel of the catheter sheath has a constant diameter.

2. The intravascular catheter and needle assembly of claim 1, wherein the catheter needle is sized between 14 and 24 gauge.

3. The intravascular catheter and needle assembly of claim 1, wherein a bottom thickness of the end for insertion of the catheter sheath is tapered from a minimum thickness to a maximum thickness.

4. The intravascular catheter and needle assembly of claim 3, wherein a top thickness of the top of the end for insertion of the catheter sheath is tapered from the minimum thickness to the maximum thickness.

5. The intravascular catheter and needle assembly of claim 4, wherein a taper of the top thickness away from the top of the end for insertion is at a greater angle than a taper of the bottom thickness away from the end for insertion.

6. The intravascular catheter and needle assembly of claim 1, wherein the end for insertion of the catheter sheath is angled between 45 and 60 degrees.

7. The intravascular catheter and needle assembly of claim 1, wherein the catheter needle has an approximate diameter of 0.027 inches multiplied by a constant, and the catheter sheath has an approximate diameter of 0.039 inches multiplied by the constant.

8. The intravascular catheter and needle assembly of claim 1, wherein the catheter sheath is composed of polyurethane.

9. A method for inserting an intravascular catheter and needle assembly, the intravascular catheter and needle assembly comprising a beveled catheter needle and a catheter sheath surrounding a portion of the catheter needle, the catheter sheath having an internal channel of the catheter sheath with a constant diameter and an end for insertion that is angled between 5 and 85 degrees, wherein the angle of the end for insertion is approximately parallel to a bevel angle of the catheter needle such that a leading edge of the catheter sheath matches a shape of the catheter needle, and wherein a top side of the catheter sheath, is tapered at approximately 18 degrees from the end for insertion and a bottom side of the catheter sheath is tapered at less than 10 degrees from the end for insertion, the method comprising:

inserting an end of the catheter needle into a blood vessel;

continuing insertion of the catheter needle into the blood vessel until the end for insertion of the catheter sheath that is angled is fully inserted into the blood vessel such that the catheter sheath is inserted within the blood vessel when the catheter needle penetrates the vessel; and withdrawing the catheter needle through the catheter sheath while the catheter sheath remains in the blood vessel.

10. The method of claim 9, wherein a bottom of the end for insertion enters the blood vessel before the top of the end for insertion.

11. The method of claim 9, wherein a bottom thickness of the bottom of the end for insertion of the catheter sheath is tapered from a minimum thickness to a maximum thickness, wherein a top thickness of the end for insertion of the catheter sheath is tapered from the minimum thickness to the maximum thickness, and a taper of the top thickness away from the end for insertion is at a greater angle than a taper of the bottom thickness away from the end for insertion.

12. The method of claim 9, further comprising refraining from rotating the catheter needle during insertion.

* * * * *